US005423861A

United States Patent [19]

Kelley

[11] Patent Number: 5,423,861

[45] Date of Patent: Jun. 13, 1995

[54] CHIROPRACTIC TREATMENT TABLE

[75] Inventor: Lawrence K. Kelley, Tacoma, Wash.

[73] Assignee: Leander Research, Manufacturing & Distributing, Inc., Port Orchard, Wash.

[21] Appl. No.: 181,571

[22] Filed: Jan. 13, 1994

[51] Int. Cl.[6] .............................................. A61F 5/00

[52] U.S. Cl. ................................... 606/241; 606/242; 606/245; 248/636; 248/615

[58] Field of Search ................................ 606/240–245; 248/638, 640, 641, 642, 636, 634, 632, 615

[56] References Cited

U.S. PATENT DOCUMENTS

| | | | |
|---|---|---|---|
| 1,261,424 | 4/1918 | Miller | 606/245 |
| 1,286,166 | 11/1918 | Albright | 606/245 |
| 3,108,465 | 10/1963 | Bochan | 248/615 X |
| 3,998,218 | 12/1976 | Lane | 606/242 |
| 4,283,004 | 8/1981 | Lamadrid | 248/615 |
| 4,842,095 | 6/1989 | Rozek | 248/615 X |
| 4,850,343 | 7/1989 | Scott | 606/245 |
| 5,028,038 | 7/1991 | De Fontenay | 248/636 X |
| 5,123,916 | 6/1992 | Riddle et al. | 606/242 X |

*Primary Examiner*—Peter A. Aschenbrenner
*Attorney, Agent, or Firm*—Price, Heneveld, Cooper, DeWitt & Litton

[57] ABSTRACT

A chiropractic table for the treatment of the muscular and skeletal cervical, thoracic, and lumbar areas of the patient's spine. The chiropractic table includes a base frame having an upright support with a table top disposed above the base frame and coupled to the upright support such that different segments of the table top may be articulated to assist in the treatment of the patient. A drive assembly is provided for reciprocating at least a portion of the chiropractic table. The drive assembly is isolated from the base frame and table top by a plurality of isolators, which attenuate the noise and vibration produced by the drive assembly while reciprocating the table top.

12 Claims, 2 Drawing Sheets

CHIROPRACTIC TREATMENT TABLE

FIELD OF THE INVENTION

The present invention relates to tables used in the chiropractic treatment of patients, and in particular to an isolation system for use in a motion-assisted flexion table.

BACKGROUND OF THE INVENTION

Chiropracty, the manipulation of the muscles and skeletal structure of the human body, has been used to treat the various maladies of the human body for some time. Various apparatus have been developed to facilitate this type of treatment, including the use of an articulated treatment table. Such tables typically include an elongated, padded platform or table on which a patient can recline. The table is further provided for a means for securing the patient's extremities, e.g., the patient's ankles and/or wrists and includes an articulated lower or anterior body section which underlies the patient adjacent the lower back. The table provides a means for raising and lowering (extension and flexion, respectively), laterally bending, rotating, and extending the anterior body section with respect to the upper body or support section. Such tables have proven to be valuable aids to the practitioner of chiropractic medicine and for patients suffering from spinal and related nerve, muscle, and skeletal disorders.

Chiropractic tables designed for conducting certain prescribed adjustments and treatments have one or more movable mechanisms which allow a section to be displaced a predetermined distance to facilitate the adjustment. Since the tables, including the separate head piece or other section, are generally provided with cushions, the cushions tend to absorb some of the forces manually applied by the health professional. One or more sections of the chiropractic table may be provided with an actuating means that will abruptly and rapidly move the cushion a controlled distance. This is often accomplished by use of a cylinder, the operating rod of which is affixed to the base of the cushion. When the cylinder is actuated by the chiropractor through suitable actuating means, the cushion will suddenly and rapidly move within a predetermined distance. When this force is applied simultaneously with the health professional manually applying a resistive force at the appropriate place on the patient, the health professional can conduct the proper spinal or body adjustment, and consistently and uniformly apply the same adjustment to that patient in future treatments as well as to other patients needing similar treatments.

One of the various treatments for patients suffering from spinal and related nerve, muscular, and skeletal maladies requires flexion of the patient's spine coupled with simultaneous manual manipulation of the spine. In performing this procedure, the magnitude, speed, and time duration of the flexion cycles is important, and variations from prescribed parameters can significantly reduce the effectiveness of the treatment. In prior devices, the magnitude, speed, and time of the flexion have been manually controlled by a practitioner utilizing his own skill and judgment. Simultaneously, a practitioner must carefully manipulate the spine to effect the desired treatment and result. This, in turn requires either the practitioner utilize one hand to produce the flexion of the table or carefully coordinate manipulation of the table by the practitioner's foot while manipulating the spinal disc by hand. Such procedures are difficult and may reduce the practitioner's effectiveness when perforating this procedure.

Chiropractic tables have been developed with an automatic mechanism which performs the cyclical flexion of the patient's spine within predetermine parameters, thereby allowing the practitioner to devote his full attention to the manual manipulation of the patient's spine. Examples of such motorized tables are disclosed in U.S. Pat. Nos. 1,938,006; 4,489,714; and 4,569,339.

A major disadvantage with prior motorized chiropractic manipulation tables is that the drive mechanism causes considerable vibration or the table and is often very noisy, causing the patient some consternation and/or annoyance during treatment. Another disadvantage is that the drive mechanism produces forces which cause fatigue failures in some components, resulting in servicing and replacement of those components.

SUMMARY OF THE INVENTION

The instant invention provides a chiropractic treatment table which provides an automatic and reliable mechanism for performing the cyclical flexion of the patient's spine. The instant invention substantially reduces unwanted vibration of the chiropractic table and the noise associated with the vibration, resulting in a more relaxed patient and effective treatment.

In one form of the invention, the chiropractic table includes a base frame having an upright support with a caudal section pivotally coupled thereto. A drive assembly is provided on the base and coupled to the caudal section for moving the caudal section up and down about the coupling with the upright support. A plurality of isolators separate the drive assembly from the base frame and the caudal section to substantially reduce the noise and vibration produced by the drive assembly.

The drive assembly for the chiropractic table includes a gearbox having a shaft extending therefrom with a crank attached to the shaft. A push rod has a first end connected to the crank. The second end of the crank is interconnected to the chiropractic table by a resilient isolator means to isolate the table from the gearbox, crank, and push rod. Likewise, a resilient isolator means is disposed beneath the gearbox such that vibration produced by the gearbox, crank, and push rod is substantially attenuated in the chiropractic table, resulting in a more quiet, peaceful, and relaxing environment during the treatment of the patient.

The advantages provided by the isolation of the drive mechanism from the chiropractic adjusting table are critical for effective treatment of the patient. The reduced vibration and noise achieved by the isolation of the drive assembly results in a much quieter environment during the treatment of the patient. The quieter environment allows the patient to fully relax allowing the health practitioner to more effectively treat and adjust the patient. Likewise, the attenuation of the vibration produced by the drive mechanism in the table also allows the patient to more completely relax and feel more comfortable on the table during the treatment. The end result is that the patient is better served by the health care professional. Furthermore, the instant invention reduces the fatigue failure of many components, resulting in less expensive service calls and longer effective life of the table.

BRIEF DESCRIPTION OF THE DRAWING FIGURES

A better understanding of the invention and the advantages provided thereby may be obtained by reference to the specification and the attached drawing figures, wherein.

DETAILED DESCRIPTION OF THE PREFERRED EMBODIMENTS

Figure 1:
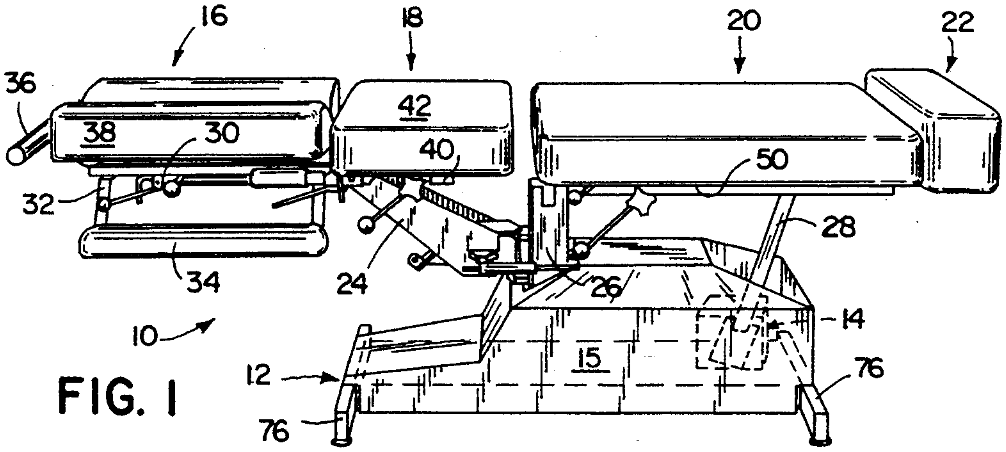
FIG. 1 is a side elevational view of one embodiment of a chiropractic table.

For the purposes of the following description, the terms "upper," "lower," "right," "left," "front," "rear," "vertical," "horizontal," and derivatives or equivalents thereof shall relate to the invention as oriented in FIG. 1. It is understood that the invention may assume various alternative orientations, except where expressly specified to the contrary. It is also understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered limiting unless the claims expressly state otherwise.

ASSEMBLY

Figure 2:
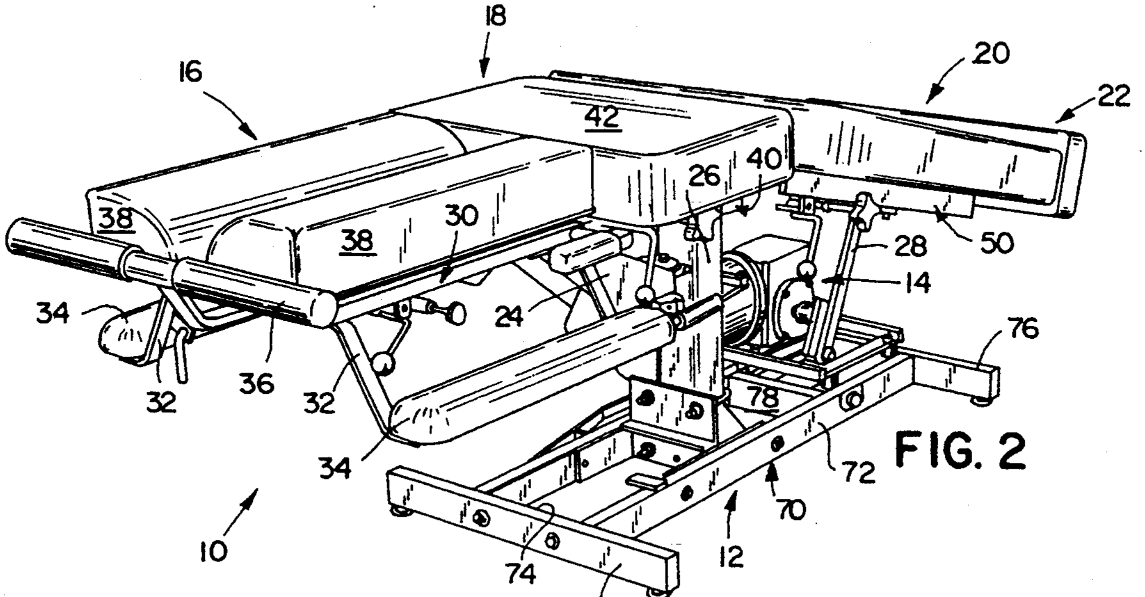
FIG. 2 is a perspective view of the table in FIG. 1.
Figure 6:
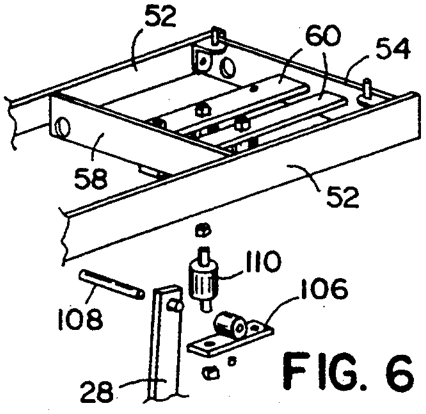
FIG. 6 is a fragmentary, perspective, exploded view illustrating the frame of the chiropractic table and a portion of the drive assembly.
Figure 7:
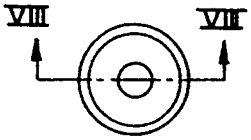
FIGS. 7 and 8 illustrate, respectively, a plan and elevational section view of one embodiment of an isolator used in association with this invention.

Referring to FIGS. 1 and 2, one embodiment of a chiropractic table 10 includes a base frame assembly 12 which contains an isolator drive assembly 14 (FIG. 2) enclosed by a cover 15. Supported above the base frame assembly 12 is a head frame assembly 16, an abdominal frame assembly 18, and a caudal frame assembly 20. Attached to the end of caudal frame assembly 20, at an end opposite that of abdominal frame assembly 18, is an ankle support assembly 22. The head and abdominal assemblies are supported above the base frame assembly 12 by a support frame 24 pivotally coupled and cantilevered from a center tube or upright support 26 extending from base frame assembly 12. The caudal assembly 20 is supported at one end by the center tube 26 and at an opposite end by a push rod 28, described in greater detail below.

Head Assembly

The head section supports the patient's cervical and upper thoracic spine. The head section is pivotally coupled along a vertical axis to the end of the support frame. The head section can also travel from approximately 37° down to approximately 24° up. A control lever under the head section controls the locking mechanism for the head section. To raise or lower the head section, the health care provider supports the front of the cushion with the palm of the hand and pulls the lever with one finger. The head section may then be lowered anywhere in the available range by moving it to that position and then releasing the lever.

Head assembly 16 includes a head frame 30 manufactured from tubular stock such as square tubular steel or aluminum stock. Depending from head frame 30 are a pair of arm rest support brackets 32, the ends of which each support arm rests 34. Extending from an end of head frame 30 opposite that abdominal assembly 18 is a T-bar assembly 36, which may be slidably adjusted depending upon the patient. Disposed on head frame 30 are a pair of cushions 38 adjacent each other with their longitudinal axis paralleling the longitudinal axis of table 10. The inner edges of each cushion have been radiused so a patient may rest his head in a face-down position in a comfortable manner and without impeding respiration. Head assembly 16 may also include one or more releases, handles, or knobs, which release and engage one or more locking devices for positioning head assembly 16 either laterally about the coupling with support frame 24 or in a vertical direction with respect to base frame assembly 12.

Abdominal Assembly

The abdominal section supports the patient's lumbar and lower thoracic spine. It typically has two operating positions: locked and lowered (floating). Whenever the table is used for flexion distraction, the abdominal section is typically in the lowered or floating position. The abdominal section is typically lowered by lifting upon an abdominal release lever located below the abdominal section.

Abdominal assembly 18 includes an abdominal frame 40, also preferably manufactured from the same tubular stock as head frame 30, and pivotally coupled at one end closest to head assembly 16 so that frame 40 may rotate about a horizontal axis transverse to the longitudinal axis of table 10. It is further preferred that the pivotal coupling with support frame 24 include a torsion spring to assist the rotational movement of the frame about the horizontal axis. The abdominal cushion 42 rests on and is attached to abdominal assembly 40 by a plurality of fasteners extending through abdominal assembly 40 into cushion 42.

The entire front section of the table, including the head and abdominal sections, can swing left or right, preferably as much as 40°. This motion is referred to as "lateral flexion." The table can be flexed laterally by grasping a handle under the head section to release the head section. The section can be moved to the appropriate location and a release of the handle locks the table in that position.

Caudal Assembly

Caudal assembly 20 includes a caudal back frame 50 including a pair of elongate, lateral side members 52 fixed at each end to a pair of end members 54 to generally define a rectangular structure. The end of frame 50 proximate abdominal assembly 18 is pivotally coupled to the uppermost end of center tube 26 by a pair of hinged tabs 56 to allow frame 50 to pivot about a horizontal axis transverse to the longitudinal axis of the chiropractic table 10. The end of back frame 50 opposite that pivotally coupled to center tube 26 includes a sub frame assembly formed by bulkhead 58 interconnecting side members 52 and at least one, and preferably two, cross-members 60 interconnecting bulkhead 58 with end member 54. End member 54 and bulkhead 58 each contain a pair of holes extending therethrough at each end to accept a pair of bars slidably disposed therein and supported in the holes by bushings, such that the ends of each of the bars extend beyond the end of frame assembly 50. The ends of the bars are interconnected by a bracket which contains threaded fasteners for attaching the ankle cushion 60 (FIGS. 1 and 2). Similar to that of head assembly 16 and abdominal assembly 18, frame 50 supports and is attached to a caudal cushion 62.

Base Frame Assembly

Figure 3:
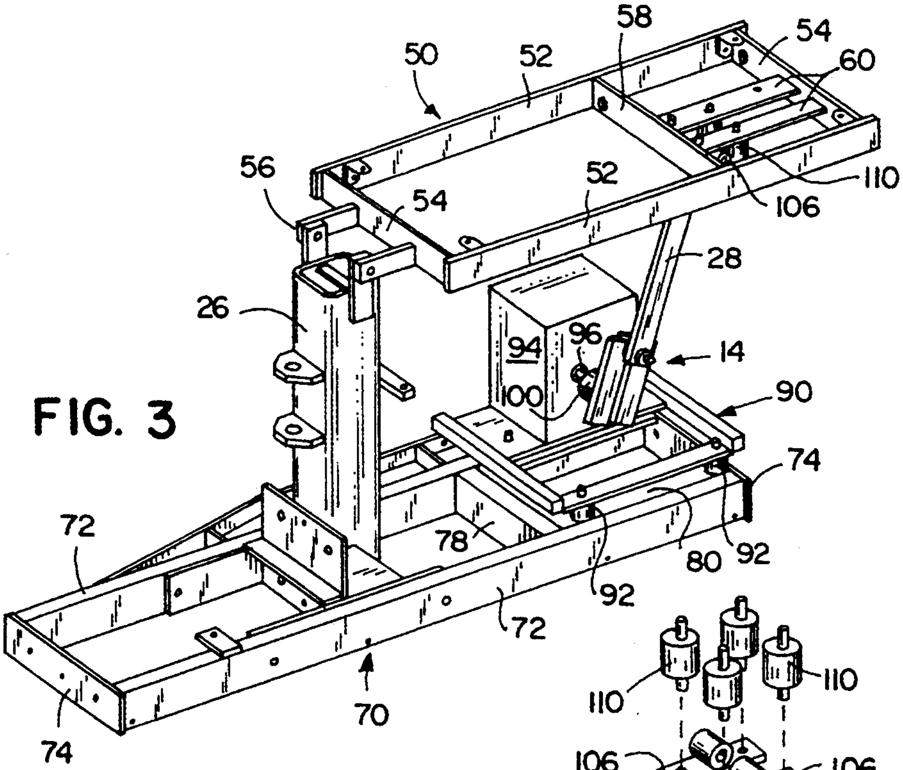
FIG. 3 is a perspective view of a portion of the chiropractic table frame.

Referring to FIGS. 2 and 3, base assembly 12 includes a frame 70 formed by a pair of elongate side members 72 interconnected at each end by end members 74. Attached to each end member 74, and extending laterally beyond side members 72, are legs 76, the ends of which receive adjustable feet for levelling the frame. The end of frame 72 beneath caudal back frame 50 includes a cross-member 78 interconnecting side members 72 which, in turn, is connected with end member 74 by a pair of angle irons or reinforcing brackets 80, each of which is located adjacent a respective side member 72.

Drive Assembly

Figure 4:
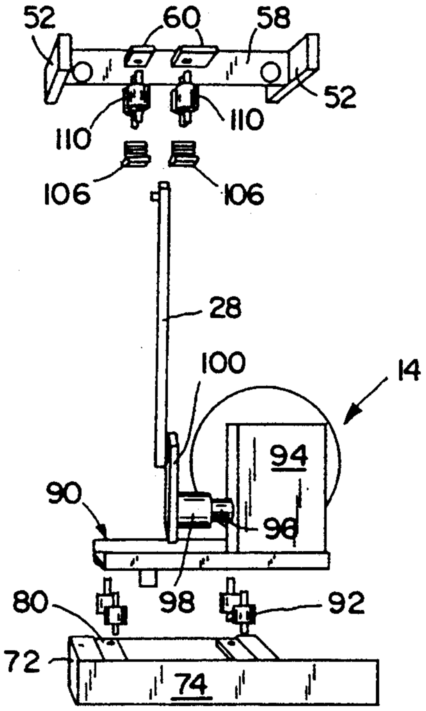
FIG. 4 is an exploded view of the drive assembly shown in association with a portion of the chiropractic table base frame.
Figure 5:
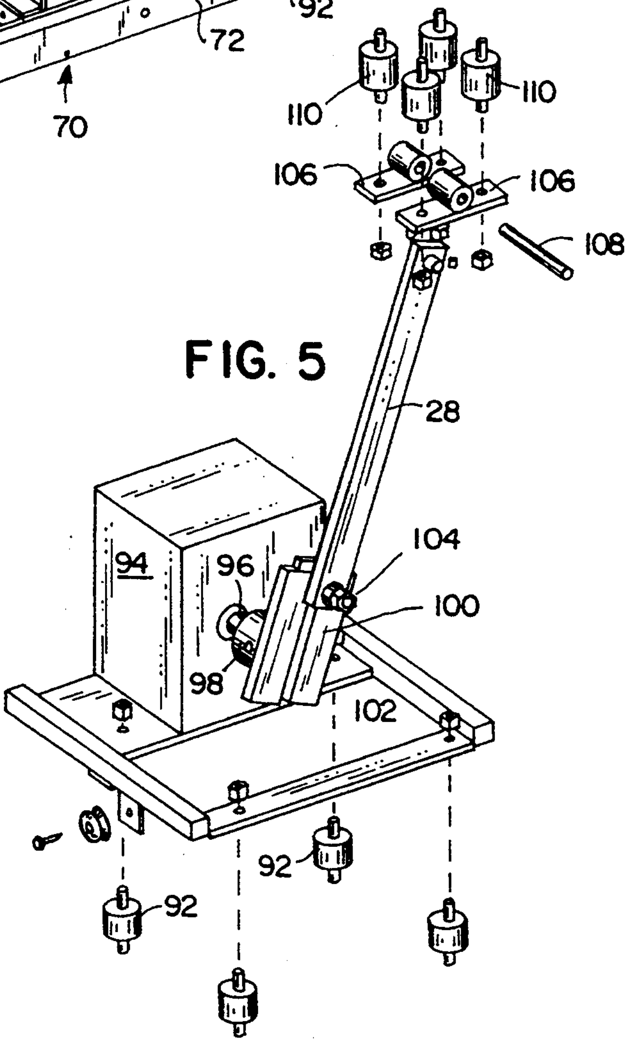
FIG. 5 is an exploded, perspective view of the drive assembly shown in FIG. 4.

Located on frame 70 and mounted to reinforcing brackets 80 is drive assembly 14 interconnected to caudal back frame 50 by push rod 28. Drive assembly 14 includes a drive plate 90 supported above and attached to reinforcing members 80 by a plurality of isolaters 92 described in greater detail below. Depending from drive plate 90 along an edge proximate cross-member 78 is a tab 88 retaining a resilient bumper 86. Tab 88 and bumper 86 are designed to engage cross-member 78 for reasons which will become apparent below. Drive plate 90 supports a transmission or gearbox 94 driven by a motor 93 shown in FIGS. 2 and 4. In one embodiment, motor 93 is a one-half horsepower AC motor such as Model 34 F241-5510 available from Baldor. Alternatively, a DC motor may be used such as Model 46304351143-OA available from MagneTek of El Paso, Tex. If the DC motor is used, it is preferably controlled by a single-phase DC motor speed control which statically converts single-phase AC line power to regulate DC power for adjustable speed armature control of permanent magnet and shunt-wound field motors. A preferred motor speed controller is the MSC700 also available from MagneTek. The motor speed control operates on 115 volts AC input and is designed for use with 90 volts DC SCR rated motors or 230 volts AC input for use with 180 volts DC SCR rated motors. Gearbox 94 is preferably art Electra-Gear Model 177 controlled backlash, right-angle worm gear available from the Electra-Gear Division of the Regal-Beloit Corporation of Anaheim, Calif.

Extending laterally from gearbox 94 is a shaft 96 which receives and is coupled to a collar 98 fixed to one end of a crank 100. Defined along the length of crank 100 in a side opposite that containing or attached to collar 98 is a longitudinal, inverted T-shaped groove 102. Groove 102 receives the head of a threaded fastener, the shaft of which extends out from crank 100 and through one end of push rod 28, which is pivotally fastened thereto by a threaded nut and bushing assembly, generally shown as 104. The opposite end of push rod 28 is pivotally coupled to cross-member 60 and the subframe assembly in caudal back frame 50 by a pair of push rod brackets 106. It is preferred that a push rod bracket 106 be located on opposite sides of push rod 28 so that a top pin 108 may extend through one push rod bracket, the end of push rod 28, and into the opposite push rod bracket on the opposite side of rod 28. Each push rod bracket 106, in turn, is coupled to cross-member 60 in caudal back frame 50 by a pair of isolators 110 as shown in FIGS. 3–6.

Figure 8:
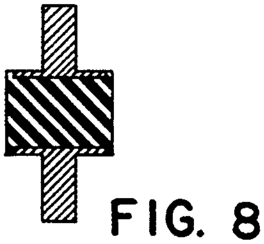

Referring to FIGS. 8 and 9, each of the isolators identified by reference numerals 92 and 110 above, include a central, cylindrical body portion 112, preferably made from a 50 Durometer natural rubber material. Although a cylindrical body is shown, other geometric forms may also be used. Located at opposite ends of body 112 are threaded T-bolts or studs 114 having a head 116 securely fastened to rubber body 112. Concentric with head 116, and extending therefrom, is the threaded shaft 118, which receives a threaded nut and lock washer to effectuate the coupling.

OPERATION

When motor 93 attached to the gearbox 94 is actuated, the rotary motion of the gearbox is translated into a cyclical movement of the crank 100. The push rod 28, attached to the crank at one end and to the caudal back frame subassembly 50 at the opposite end, raises and lowers the caudal assembly 20 about pivot axis 56. Groove 102 in crank 100 allows for manual adjustment of the table's depth of flexion. To decrease or increase the depth of flexion, it is preferred to stop the motor 93 when caudal assembly 20 is mid-way through its travel. Slotted crank 100 is in a horizontal position. After positioning the table mid-way through its stroke, tile nut at the end of the fastener 104 is loosened, allowing the head in tile groove 102 to move. Moving the end of the push rod 28 toward shaft 96 of the gearbox 94 decreases the amplitude of the cyclical movement of the crank, resulting in a decreased depth of flexion. Moving the end of the push rod 28 to the end of the crank 100 furthest from the shaft of the gearbox results in the maximum flexion amplitude.

As the crank 100 moves in the upward direction to raise caudal assembly 20, drive plate 90 is forced in a direction toward center or upright support tube 26, while brackets 106 are forced in a direction toward end member 54 and away from upright support tube 26. Conversely, as crank 100 begins to descend and lower caudal back frame 50, mounting plate 90 is allowed in an opposite direction away from upright support tube 26, while brackets 106 are allowed in a direction toward cross-member 58 and upright support tube 26. These reciprocating sheer forces exerted upon the drive plate 90 and push rod brackets 106 are in essence absorbed by resilient isolators 92 and 110.

When the chiropractic table supports the patient and the automated, motorized flexion distraction feature of the table is used, the weight of the patient imparts a greater sheer force on isolators 92 when the caudal assembly 20 is raised. Bumper 86, dependent from drive plate 90, engages cross-member 78 to assist isolators 92 and fix drive assembly 14 in position. When the drive assembly is activated to lower the caudal assembly 20, the sheer force on isolator members 92 is substantially reduced to the point where the crank reaches its downward apogee when the sheer force is again re-exerted on the drive plate 90. Bumper 86 and isolator members 92, 110 absorb a substantial amount of the force produced by the raising and lowering of caudal assembly 20, thus resulting in less vibration of chiropractic table 10 during operation. Also as a direct result, the operation of the automated, motorized flexion distraction feature of the chiropractic table is quieter as a result of the stresses being absorbed by the isolators 92, 110. The net effect is a relaxed patient and a more effective treatment by the health care provider.

The above description is considered that of the preferred embodiments only. Modification of the invention will occur to those skilled in the art and to those who make and use the invention. Therefore, it is understood that the embodiments shown in the drawings and described above are merely for illustrative purposes and are not intended to limit the scope of the invention, which is defined by the following claims.

The embodiments of the invention in which an exclusive property or privilege is claimed are defined as follows:

1. A chiropractic table, comprising:
- a base frame having an upright support;
- a table top disposed above said base frame and attached to said upright support, said table top having a head frame, an abdominal frame, and a caudal frame;
- a drive assembly coupled to said caudal frame for moving said caudal frame with respect to said upright support, said drive assembly including a transmission having an output shaft, a motor for driving said input shaft of said transmission, a crank attached to said output shaft, and a push rod having a first end pivotally coupled to said crank and an opposite end pivotally interconnected to said caudal frame; and
- an isolator assembly interconnecting said drive assembly to said base frame and said caudal frame to said push rod for substantially reducing noise and vibration, said isolator assembly including at least one push rod bracket member located adjacent one end of said push rod opposite to said crank; said end of said push rod and said push rod bracket interconnected by a pin, and a plurality of resilient members interconnecting said push rod bracket to said caudal frame.

2. The chiropractic table as defined in claim 1, wherein said caudal frame is pivotally coupled at one point to said upright support and at a second point to said drive assembly.

3. The chiropractic table as defined in claim 2, wherein said isolator assembly includes:
- a drive plate disposed beneath said drive assembly; and
- a plurality of resilient connectors interconnecting said drive plate to said base frame.

4. The chiropractic table as defined in claim 3, wherein said resilient connectors include:
- a resilient polymeric body member; and
- at least one attachment member rigidly fixed to said body member, and having a fastening portion extending therefrom for making a connection with an adjacent component.

5. The chiropractic table as defined in claim 4, further including a 50 Durometer natural rubber body member and a pair of studs, each having a head securely fastened to said body member and a threaded shaft extending therefrom.

6. A chiropractic table, comprising:
- a base frame having an upright support extending therefrom;
- a caudal section pivotally coupled to said upright support, said caudal section having a back frame having a pair of generally parallel side members interconnected to each other at each end by a pair of end members to define a generally rectangular structure, one end member of said back frame pivotally coupled to said upright support, a subframe assembly attached to said back frame opposite said end member coupled to said upright support, said subframe including at least one bulkhead located between said end members and interconnected to said side members, and at least one cross-member interconnecting said bulkhead to said end member opposite that pivotally coupled to said upright support, and a cushion disposed on top of said back frame for receiving a patient;
- a drive assembly on said base frame and coupled to said caudal section for moving said caudal unit up and down about the coupling of the caudal section to said upright support; and
- a plurality of isolators interconnecting the drive assembly to said base frame and said caudal section for substantially reducing noise and vibration produced by said drive assembly, each of said plurality of isolators including a flexible polymeric body interconnecting said drive assembly to said base frame and said caudal section, said polymeric body absorbing tensional, compressional, and sheer forces exerted on said base frame and said caudal section by said drive assembly; and
- at least one stud fastener having a lead portion retained against said polymeric body with a threaded shaft extending from said head portion and receiving a correspondingly threaded nut to make the connection.

7. The chiropractic table as defined in claim 6, further including:
- a head section pivotally coupled to said upright support at an end of said table opposite said caudal section, said head section adapted to support a patient's cervical upper thoracic spine; and
- an abdominal section pivotally coupled to said upright support between said head section and said caudal section and adapted to support a patient's lumbar and lower thoracic spine.

8. The chiropractic table as defined in claim 6, wherein said drive assembly includes:
- a gearbox having a base interconnected to said base frame by said isolators, and a shaft extending from said gearbox;
- a crank attached to said shaft; and
- a push rod having a first end connected to said crank and a second end connected to said caudal section.

9. The chiropractic table as defined in claim 8, wherein said polymeric body is formed from a natural rubber into a predetermined shape and having a Durometer hardness between 30 and 70.

10. The chiropractic table as defined in claim 8, further including:
- a motor coupled in drive relation to said gearbox for driving said crank and push rod at a speed other than that produced by said motor; and
- a motor speed controller circuit operably coupled to said motor for manually and automatically controlling said motor.

11. The chiropractic table as defined in claim 8, further including a bumper assembly extending from said base of said gearbox and adapted to engage a static point for limiting translational movement of said gearbox and base while reciprocating said caudal section of the chiropractic table.

12. A chiropractic table, comprising:

a base frame having an upright support extending therefrom;

a caudal section pivotally coupled to said upright support;

a drive assembly on said base frame and coupled to said caudal section for moving said caudal section up and down about the coupling of the caudal section to said upright support;

a plurality of isolators interconnecting said drive assembly to said base frame and said caudal section for substantially reducing noise and vibration produced by said drive assembly, each of said plurality of isolators including a flexible polymeric body interconnecting said drive assembly to said base frame and said caudal section, said polymeric body absorbing tensional, compressional, and shear forces exerted on said base frame and said caudal section by said drive assembly; and at least one stud fastener having a head portion retained against said polymeric body with a threaded shaft extending from said head portion and receiving a correspondingly threaded nut to make the connection.

* * * * *

UNITED STATES PATENT AND TRADEMARK OFFICE

CERTIFICATE OF CORRECTION

PATENT NO. : 5,423,861

DATED : June 13, 1995

INVENTOR(S) : Lawrence K. Kelley

It is certified that error appears in the above-indentified patent and that said Letters Patent is hereby corrected as shown below:

Column 2, line 3
"perforating" should be --performing--;

Column 5, line 48
"art" should be --an--;

Column 6, line 28
"tile" should be --the--; and

Column 6, line 30
"tile" should be --the--.

Signed and Sealed this

Fourteenth Day of May, 1996

*Attest:*

Bruce Lehman

BRUCE LEHMAN

*Attesting Officer* *Commissioner of Patents and Trademarks*